United States Patent [19]
Yallampalli et al.

[11] Patent Number: 6,133,320
[45] Date of Patent: Oct. 17, 2000

[54] TREATMENT OF OSTEOPOROSIS AND METABOLIC BONE DISORDERS WITH NITRIC OXIDE SUBSTRATE AND/OR DONORS

[75] Inventors: Chandrasekhar Yallampalli, Houston; Sunil J. Wimalawansa, Friendswood, both of Tex.

[73] Assignee: Board of Regents, The University of Texas System

[21] Appl. No.: 09/177,978

[22] Filed: Oct. 22, 1998

Related U.S. Application Data

[62] Division of application No. 08/616,470, Mar. 19, 1996, Pat. No. 5,898,038.

[51] Int. Cl.$^7$ .......................... A61K 31/155; A61K 31/04
[52] U.S. Cl. ........................ 514/632; 514/634; 514/742
[58] Field of Search ........................... 514/632, 634, 514/742

[56] References Cited

U.S. PATENT DOCUMENTS

| | | | |
|---|---|---|---|
| 4,393,226 | 7/1983 | Witiak et al. | 549/433 |
| 5,364,841 | 11/1994 | Cooper et al. | 514/12 |
| 5,622,973 | 4/1997 | Morriello et al. | 514/318 |

FOREIGN PATENT DOCUMENTS

| | | |
|---|---|---|
| WO 95/02408 | 1/1995 | WIPO . |
| WO 95/13800 | 5/1995 | WIPO . |
| WO 95/13802 | 5/1995 | WIPO . |

OTHER PUBLICATIONS

Kasten et al. "Potentiation of osteoclast . . . Synthase" Soc. Natl. Acad.Sci. USA vol. 91, pp. 3569–3573 (1994).

Visser et al. "Arginine . . . Osteoporosis" Medical Hypotheses vol. 43, pp. 339–342. (1994).

Wimalawansa et al., "Nitric Oxide Donor Alleviates Ovariectomy–Induced Bone Loss," *Bone*, 18(4):301–304, 1996.

Wimalawansa et al., "Replacement Therapy with Nitric Oxide or Nitric Oxide Dornor In Vivo, Maintains the Bone Mass in Rats After Ovariectomy," *World congress on Osteopororis*, Abstract No.PTU 759, Amsterdam, May 18–23, 1996.

Wimalawansa, "Steroid–Induced Osteoporosis can be Prevented with Nitric Oxide," *American Society for Bone and Mineral Research*, Sep. 7–11, 1996.

Yallampalli et al., "Calcitonin Gene–Related Peptide Reverses the Hypertension and Significantly Decreases the Fetal Mortality in Pre–Eclampsia Rats Induced by $N^G$–Nitro–L–Arginine Methyl Ester," *Human Reproduction*, 11(4):895–899, 1996.

*Primary Examiner*—Theodore J. Criares
*Attorney, Agent, or Firm*—Fulbright & Jaworski

[57] ABSTRACT

Primary and secondary osteoporosis in a female or a male mammal is treated by administering thereto a nitric oxide synthase substrate, a nitric oxide donor or both, optionally; in further combination with one or more of an estrogen, a progestin, an anabolic steroid. Nitric oxide substrate or donor also can be combined with one or more of other medications acting on bone, such as bisphosphonate, calcitonin, fluoride, androgen and other novel therapeutic agents. Either nitric oxide donor or substrate by itself or combination with other medications as described above can be used in both women and men, (preferably human) for prevention and treatment of osteoporosis and other metabolic bone disorders.

98 Claims, 2 Drawing Sheets

TREATMENT OF OSTEOPOROSIS AND METABOLIC BONE DISORDERS WITH NITRIC OXIDE SUBSTRATE AND/OR DONORS

This is a divisional of application Ser. No. 08/616,470, filed Mar. 19, 1996, now U.S. Pat. No. 5,898,038.

BACKGROUND OF THE INVENTION

This invention relates to a new method for treatment of osteoporosis and bone mineral disorders and to prevent bone loss, fractures and other abnormal clotting patterns, urogenital discomfort, prevention and treatment of cardiovascular diseases, and other conditions associated with the reduction in ovarian function in middle-aged women, with a nitric oxide synthase substrate (L-arginine), a nitric oxide donor, or both, alone or in combination with an estrogen and/or a progestin. Same compounds are also useful in men to decrease bone turnover and hence prevention and treatment of osteoporosis and for treatment of other metabolic bone disorders.

It is now well known, that hormone replacement therapy, such as estrogen treatment, improves or reverses the adverse effects of the cessation of sex steroid secretion by the ovaries during menopause. Estrogens have also been shown to prevent bone loss and improve a variety of functions including mood and psychological well-being in postmenopausal women. Estrogens have been shown to effect arterial tone and this may help to explain the reduction in hot flushes and decrease the cardiovascular mobility and mortality in postmenopausal women with estrogen replacement therapy. Unopposed estrogen therapy in postmenopausal women has been associated with endometrial hyperplasia and endometrial cancer.

Many studies have shown that the addition of progesterone to estrogen replacement therapy decreases the risk of endometrial cancer and even reverses endometrial hyperplasia. However, progestins are not without untoward side effects. Progestins may oppose the beneficial effects of estrogens on the cardiovascular system by inducing an adverse lipid profile in circulation. Progesterone may also counteract the beneficial effects of estrogen on vascular walls. Moreover, irregular or withdrawal bleedings are common with combined estrogen-progestin therapy. The current hormone replacement therapy (HRT) employs combinations of estrogen and progestins as in the case of most contraceptives.

One of the most exciting recent advances in biology and medicine is the discovery that nitric oxide which is produced by endothelial cells (as one of the endothelial derived relaxing factors) and that it is involved in the regulation of vascular tone, platelet aggregation, neurotransmission and immune activation in a favorable fashion (Furchgott and Zawaszki, 1980; Moncada, Palmer and Higgs, 1991; Ignarro, 1991). Nitric oxide is an important mediator of relaxation of the vascular smooth muscle (Moncada, Palmer and Higgs, 1991), was formerly known as EDRF (endothelin-derived relaxing factor) (Furchgott and Zawaszki, 1980; Moncada, Palmer and Higgs, 1991). Nitric oxide is synthesized by the oxidative deamination of a guanidino nitrogen of L-arginine by at least different isoforms of a flavin-containing enzyme, nitric oxide synthase (Moncada, Palmer and Higgs, 1991). Synthesis of nitric oxide has been shown to be competitively inhibited by analogues of L-arginine; $N^G$-nitro-L-arginine methyl ester (L-NAME), $N^G$-monoethyl-L-arginine (LMMA), N-iminoethyl-L-arnithine (L-NIO), L-monomethyl-L-arginine (L-NNMA) and L-$N^G$-methylarginine (LNMA) and Nw-nitro-L-arginine (L-NA).

Nitric oxide elevates levels of cGMP (1,3,5-cyclic guanosine monophosphate) within the vascular smooth muscle to produce relaxation and to reduce blood vessels tone (Moncada, Palmer and Higgs, 1991). Nitric oxide is also produced by macrophages and other immune cells. Nitric oxide binds to heme molecules and activates soluble guanylate cyclase (Ignarro, 1991) to increase the intracellular content of cGMP. It has long been recognized that nitrovasodilators, such as nitroprusside and nitroglycerine, inhibit vascular smooth muscle contractility to produce relaxation or to reduce vascular tone. These agents have been used since the late 1800's as vasodilators. However, only recently has the mechanism of action of these compounds been realized. Nitrovasodilators are now classified as nitric oxide donors because they are metabolized at the sites of interests to release nitric oxide (Moncada, Palmer and Higgs, 1991). The long-term use of nitrovasodilators may be regarded as substitution or a replacement therapy for a failing physiological mechanism.

There is a substantial body of evidence from animal studies that a deficiency in nitric oxide contributes to the pathogenesis of several diseases including hypertension, atherosclerosis and diabetes (Moncada, Palmer and Higgs, 1991) and toxemia of pregnancy (Yallampalli et al., 1993). There are many recent studies showing that the inhibition of nitric oxide synthase dramatically increases blood pressure. For example, the inhibition of nitric oxide synthesis with L-NNMA, L-NA or L-NAME leads to elevation of blood pressure and suggests that reduction of NO may contribute to the pathogenesis of hypertension (Moncada and Palmer, 1992). Furthermore, L-NAME-treatment potentiates the presser responses to angiotension, blunting of the release of nitric oxide by umbilical vessels (Pinto et al., 1991). The physiological decrease in blood pressure in pregnant spontaneous hypertensive rats was also shown to depend on endothelial derived nitric oxide (Ahokas, Merces and Sibal, 1991). Additionally, infusion of L-NA increases blood-pressure in pregnant rats and potentiates responses to vasopressors (Molnar and Hertelendy, 1992). These studies suggest that impaired nitric oxide synthesis may be an important mechanism in the etiology of several cardiovascular dysfunctions.

Nitric oxide synthesis and nitric oxide effector system (cGMP-dependent relaxation mechanism) are thought to be regulated by steroid hormones. There is an increase in cardiovascular diseases in women following menopause and these might be related to the decrease in sex steroids and thereby an alteration in nitric oxide. Female steroid hormones have been shown to modulate endothelium-dependent relaxation of vascular smooth muscle via nitric oxide. Estradiol treatment of rats causes increased nitric oxide production by vascular tissues, whereas progesterone counteracts this phenomenon (Miller and Van Houtte, 1991). It is well known that pregnancy is associated with an increase in cardiac output and a decrease in the resistance of virtually all the vascular beds in the body, although the mechanism of this phenomenon is not known. It is possible that this may be associated with changes in nitric oxide production or effects as a result of elevated steroid hormone levels. One important observation with regard to the above mechanism is that antiprogestins elevate blood pressure in animals and they produce hot flushes in humans, both males and females. The hot flushes may be mediated by the inadequate steroid action on the release of nitric oxide. Hot flushes are a primary symptom in menopausal, postmenopausal women and they are relieved by both estrogen and progesterone.

Studies described herein (see below) show that nitric oxide and the subsequent relaxation of the uterus is controlled by progesterone. The relaxation effects of the nitric oxide substrate, L-arginine, are greater in late pregnancy when progesterone levels are elevated in pregnant rats. Also there is greater uterine relaxation with L-arginine when uterine strips are taken from nonpregnant, ovariectomized rats treated with progesterone. In addition, treatment with pregnant rats with the nitric oxide inhibitor produces signs and symptoms of preeclampsia (e.g. hypertension, fetal retardation and proteinurea—the classical triad of preeclampsia). These symptoms are related to the decrease in vascular resistance and placental perfusion. Preeclampsia is also a well known model of accelerated atherosclerosis, as the decrease in placental perfusion is accompanied by increased fibrin deposition in placental vessels and increased thrombus formation.

EP 0441 119 A2 mentions the use of L-arginine in the treatment of hypertension and other vascular disorders. It suggests that the mechanism by which L-arginine is effective for this purpose is because it may be the physiological precursor of "the most powerful endothelial-derived releasing factor, nitric oxide". The use of L-arginine in combination with other pharmaceutically active agents is not discussed in EP 0441 119 A2 publication.

This invention is also applicable to both primary and secondary osteoporosis in both females and males. In the female, the method of choice of treatment of primary osteoporosis is estrogen replacement therapy and in the case of male, the method of choice of treatment of primary osteoporosis is androgen replacement therapy. In both sexes for the secondary osteoporosis the underlying causative factors are numerous, including medication-induced osteoporosis (e.g., corticosteroids, antiepileptics, anticoagulants, thyroxine), immunosuppressant agents used in prevention of graft rejection and other disorders (cyclosporin), malignancies (e.g., multiple myeloma), immobilization-induced bone loss and other conditions of bone loss.

One aspect of the present invention provides a method for the prevention and treatment of primary and secondary osteoporosis, including medication induced-osteoporosis (i.e. corticosteroid-induced osteoporosis) and other metabolic bone disorders with a nitric oxide substrate and/or donor.

It is another object to provide such a method in which a progestational agent is used in combination with a nitric oxide substrate and/or donor for the prevention and treatment of osteoporosis and other metabolic bone disorders.

It is a further object to provide a method for the prevention and treatment of osteoporosis and other metabolic bone disorders using an estrogenic agent in combination with a nitric oxide substrate and/or donor.

It is another object to provide a method for prevention and treatment of osteoporosis and other metabolic bone disorders using a combination of an estrogenic agent and progestational agent with a nitric oxide substrate and/or donor.

Another object is to provide a method of prevention and treatment of male primary and secondary osteoporosis and other metabolic bone disorders using nitric oxide substrate and/or donor.

A further object is the provision of pharmaceutical compositions useful in practicing the methods of this invention.

Other objects will be apparent to those skilled in the art to which this invention pertains. Another object is to provide a method of prevention and treatment of male primary and secondary osteoporosis and other metabolic bone disorders using nitric oxide substrate and/or donor.

SUMMARY OF THE INVENTION

An important embodiment of this invention relates to a method of treating osteoporosis or other metabolic bone disorders in a menopausal or postmenopausal female. This embodiment comprises administering to a female manifesting the symptoms thereof, one or both of a nitric oxide synthase substrate, particlularly L-arginine and/or a nitric oxide donor, alone or in further combination with one or more of an estrogen, and a progestin in amounts effective to ameliorate osteoporosis symptoms. The amount of the estrogen is bioequivalent to approximately 2 mg per day of estradiol and the amount of the progestational agent administered is bioequivalent to 50–300 mg of injected progesterone. The amount of the nitric oxide synthase substrate (L-arginine), nitric oxide donor or both is effective to, respectively, either raise the blood level of circulating L-arginine in a patient to whom the composition is administered to at least about 10–50 nmole above the normally 50–100 nmole circulating levels or provide nitric oxide donor levels of about 1–1000 nM (varying according to the particular donor). This invention also relates to use of L-arginine or nitric oxide donor compounds in prevention and treatment of primary osteoporosis in men and in both sexes, secondary osteoporosis, including medication-induced osteoporosis (e.g., corticosteroid-induced osteoporosis) and other metabolic bone disorders. L-arginine is the only acknowledged substrate of nitric oxide synthase but any analogous substrates behaving in a similar manner are viewed as equivalent.

In a product aspect, this invention relates to a pharmaceutical composition comprising at least one of a nitric oxide synthase substrate such as L-arginine and a nitric oxide donor, alone or in further combination with one or more of a estrogen and/or progestin. The amount of the estrogen is bioequivalent to about 2 mg of estradiol. The amount of the progestin is bioequivalent to 50–300 mg. of injected progesterone. The amount of L-arginine per unit dosage is effective to either raise blood level of circulating L-arginine to at least about 1 nM above the normally 2–3 nM circulating levels. The nitric oxide donor lends are enough to raise the nitric oxide levels to about 1 to 1000 nM.

DESCRIPTION OF PREFERRED EMBODIMENTS

The methods of this invention to treat osteoporosis and other bone mineral disorders in a menopausal/postmenopausal manunal and in men, preferably a human, who is manifesting the signs and/or symptoms or both (i.e. treatment of osteoporosis) thereof or who is a high risk candidate (prevention of osteoporosis) for doing so, e.g., as determined by appropriate clinical conditions.

Because these abnormal conditions of bone loss and other metabolic bone diseases in both sexes are produced by or aggravated by subnormal nitric oxide synthesis, both nitric oxide synthase substrate and donors, (e.g., L-arginine, and nitric oxide donors, e.g., sodium nitroprusside, nitroprusside, nitroglycerine, SIN-1, isosorbid mononitrate and isosorbid dinitrate) are useful for ameliorating the symptoms thereof and, in one aspect of the method of this invention, a combination of both are employed.

In the case of female, for both primary and secondary osteoporosis an added effect is achieved when the nitric oxide substrate and/or nitric acid donor is administered concurrently with an estrogen and/or progestational agent. Thus, the method aspect of this invention and the pharmaceutical composition aspect of this invention employs a nitric oxide donor and/or a nitric oxide synthase substrate such as L-arginine individually or together with an estrogen and/or a progestin, progesterone or norgestrel, or other agents that affect bone metabolism including bisphosponates, calcitonin, fluoride.

In the case of a male, for both primary and secondary osteoporosis, an added effect is achieved when the L-arginine and/or nitric oxide donor is administered concurrently with an androgen. Thus, the method aspect of this invention and the pharmacological composition aspect of this invention employs one or both of a nitric oxide donor and a nitric oxide synthase substrate with an androgen or other agents that affect bone metabolism such as, e.g., bisphosphonates, calcitonin, fluoride, and anabolic steroids.

Examples or combinations of active agents which can be administered concurrently with a nitric oxide substrate and/or nitric oxide donor are estrogens and progestins (see below).

Examples of dosage ranges of typical NO-substrates and NO-donors (per os) are:

|  | Total dose |
| --- | --- |
| L-Arginine | 500 mg - 10 g p.o. |
| Sodium Nitroprusside | range 500–2000 ug/kg/day |
| Nitroglycerine | 0.5–10 mg |
| Isosorbid mononitrate | 10–100 mg |
| Isosorbid dinitrate | 10–100 mg |

The following are typical oral dosage ranges of active agents of the estrogen and progestin with the nitric oxide substrate or donor:

Estrogens: a daily dose bioequivalent to about 1 to 2 mg per day, e.g., Premarin R, Wyeth-Ayerst, 0.625 mg/day, estradiol valerate, 50 ug/day transdermally, vaginal estradiol creams, 1.25 mg/day and vaginal estradiol rings, 0.2 mg/day.

Progestins: A daily dose bioequivalent to 50–300 mg of progesterone/day, e.g., an injectable suspension of medroxyprogesterone acetate to provide a weekly dose of thereof of 100–1000 mg or tablets or dragees providing an oral dose thereof of 5–10 mg/day, an injectable solution of hydroxyprogesterone caproate which provides a weekly dose of 250–500 mg; tablets, capsules or dragees of northindrone acetate which provide a daily dose of 5–20 mg.

Other examples of estrogens and progestins are listed below:

Oral "natural" estrogens used in hormone replacement therapy currently available in the UK.

| Product | Composition | Dose (mg per day) |
| --- | --- | --- |
| Climaval (Sandoz) | Estradiol valerate | 1 or 2 |
| Progynova (Schering) | Estradiol valerate | 1 or 2 |
| Harmogen (Abbott) | Piperazine oestrone sulfate | 1.5 or 2.5 |
| Hormonin (Shire) | Estradiol + Estrone + Estriol | 0.6 |
| Premarin (Wyeth-Ayers) | Conjugated Estrogens | equine 0.625 or 1.25 or 2.5 |

Commercially available combination calendar packs or hormone replacement therapy.

| Product | Generic composition |
| --- | --- |
| Estrapak | Estradiol 50 μg per day (28 days, 8 patches) |
| Prempak-C | + |
| Trisequens | Norethisterone acetate 1 mg per day (12 days) |
| Trisequens forte | conjugated equine oestrogens 0.625 mg per day (28 days) + |
| Cyclo-progynova | Norgestrel 0.15 mg per day (12 days) conjugated equine oestrogens 1.25 mg per day (28 days) + |
|  | Norgestrel 0.15 mg per day (12 days) |
|  | Estradiol 2 mg per day + oestriol 1 mg per day (22 days) + |
|  | Norethisterone acetate 1 mg per day (10 days) |
|  | Estradiol 2 mg per day + oestriol 0.5 mg per day (6 days) |
|  | Estradiol 4 mg per day + oestriol 2 mg per day (22 days) + |
|  | Norethisterone acetate 1 mg per day (10 days) |
|  | Estradiol 1 mg per day + oestriol 0.5 mg per day (6 days) |
|  | Estradiol valerate 1 mg per day (21 days) + |
|  | Levonorgestrel 0.25 mg per day (10 days) |
|  | Estradiol valerate 2 mg per day (21 days) + |
|  | Levonorgestrel 0.5 mg per day (10 days) |

Daily doses of progestogens taken for 12 days per month in patients receiving oral or transdermal estrogens.

| Norethisterone | 0.7–2.5 mg per day |
| --- | --- |
| Medroxyprogesterone acetate | 10 mg per day |
| Norgestrel | 150 μg per day |
| Dydrogesterone | 10–20 mg per day |

Bisphosphonates:
Any of the available pharmaceutical preparations of bisphosphonates, i.e. Disodium etidronate 5–10 mg/kg BWt for 14 days in every 90 days, Alendronate 10 mg, once daily and other newer preparations such as Pamidronate, Clodronate, and Residronate.

Calcitonin:
Any of the available pharmaceutical preparations of calcitonin, i.e. salmon, eel or human calcitonins, dosage range 10–200 i.u., daily, parenteral or nasal route.

Anabolic steroids:
Any of the available pharmaceutical preparations of anabolic steroids, i.e. Nondrolone decaonate 50 mg. 1/M injection every 3 weeks.

Androgens:
Any of the available pharmaceutical preparations of Testosterone (100 mg, 1/M, monthly) or its analogs.

Fluoride:
Any of the available pharmaceutical preparations of fluoride, e.g., sodium fluoride, 10–50 mg, once daily.

The pharmacologically active agents employed in this invention can be administered in admixture with conventional excipients, i.e., pharmaceutically acceptable liquid, semi-liquid or solid organic or inorganic carriers suitable, e.g., for parenteral or enteral application and which do not deleteriously react with the active compound in admixture therewith. Suitable pharmaceutically acceptable carriers include but are not limited to water, salt solutions, alcohols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc.

The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqeous solutions, as well as suspensions, emulsions, depot preparations or implants, including suppositories, creams, ointments, and transdermal patches.

In a preferred aspect, the composition of this invention is adapted for ingestion. For enteral application, particularly suitable are unit dosage forms, e.g., tablets, dragees or capsules having talc and/or a carbohydrate carrier or binder of the like, the carrier preferable being lactose and/or corn starch and/or potato starch; particulate solids, e.g., granules; and liquids and semi-liquids, e.g., syrups and elixirs or the like, wherein a sweetened vehicle is employed. Sustained release compositions can be formulated including those wherein the active compound is protected with differentially degradable coatings, e.g., by microencapsulation, multiple coatings, etc.

Suitable for oral administration are, inter alia, tablets, dragees, capsules, pills, granules, suspensions and solutions. Each unit dose, e.g., each tablespoon of liquid or each tablet, or dragee contains, for example, 0.1–1000 mg of each active agent.

Solutions for parenteral administration contain, for example, 0.01–1% of each active agent in an aqueous or alcoholic solution.

The nitric oxide substrate and/or donor can be administered as an admixture with agents described above and any other optional active agent of as a separate unit dosage form, either simultaneously therewith or at different times during the day from each other.

The combination of active agents is preferably administered at least once daily (unless administered in a dosage form which delivers the active agents continuously) and more preferably several times daily, e.g., in 2 to 6 divided doses. The typical dose is about 0.5 to 1000 mg of each active agent, although some less active agents, e.g., L-Arginine, require much higher oral dosages, e.g., 500 to 10,000 mg, and others, e.g., sodium nitroprusside, require lower doses, e.g., 500–2000 ug/kg/day. Doses for nitroglycerine typically are orally 2.5 mg 2× daily; sublingually, 0.8 mg 1–4× daily; and transdermally via patch or cream, 0.2–0.4 mg/hr. Since the LD 50 dosages of most of these active agents is known in the prior art, a lower dosage regimen can be initiated and the dosage increased until a positive effect is achieved or a higher dosage regimen can initially be employed, e.g., in a crisis situation, and the dosages regulated downward as relief from the symptoms is achieved. Combinations of agents can be employed either continuously or sequentially.

In humans, L-arginine, estradiol, and progesterone (or bioequivalent of another progestin) should be given in a ratio which produces blood plasma levels of about 50–200 nmolar L-arginine, 500 to 1000 nmolar of estradiol, and 30–100 nmolar progesterone.

Figure 1:
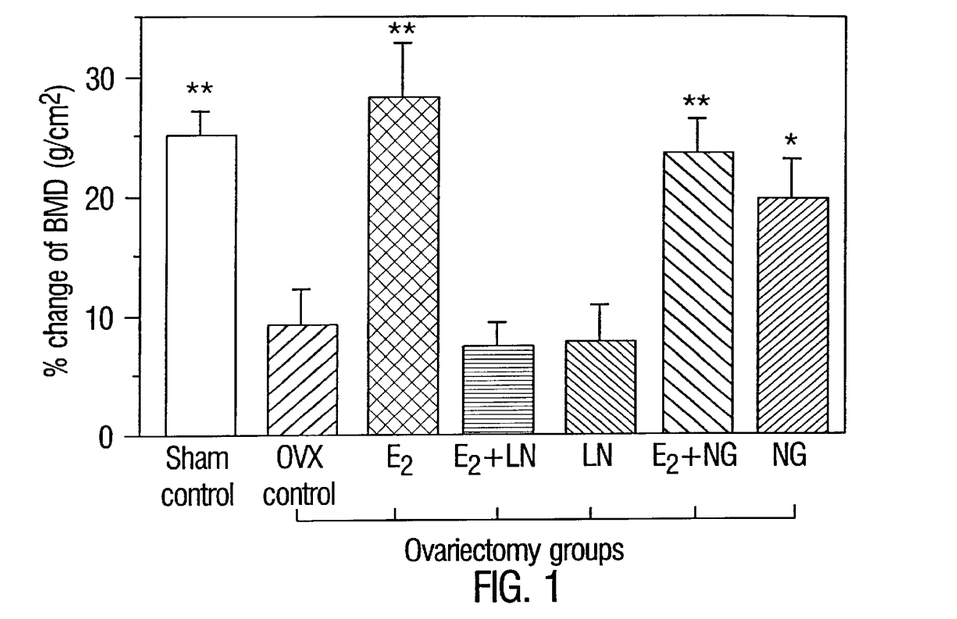
FIG. 1 illustrates the percentage changes of bone mineral density 6 weeks after each therapy as determined by dual energy x-ray absorptiometric bone scan of vertebrae.

FIG. 1 illustrates the percentage changes of bone mineral density (BMD) 6 weeks after each therapy as determined by dual energy x-ray absorptiometric bone scan (DXA) of vertebrae. OVX=ovariectomy, $E_2$=estrogen treated, LN=L-NAME treated, NG=nitroglycerine treated. Values are mean±SEM for 5 animals per group. Comparisons were made against ovariectomized rats (reference, OVX control) * P<0.05, * * P<0.02. For between group comparison the changes of BMD were calculated from the baseline measurements and expressed as percentages. As expected, the increase in BMD over the 6 week period in OVX rats was substantially lower (P<0.02) than control sham-operated animals. Supplementation with $E_2$ completely reversed the effects of OVX on BMD, and the BMD was similar to that seen in sham-operated rats (i.e., control group). The addition of L-NAME was no further detrimental to the reduction in bone mass in OVX rats. However, the supplementation of $E_2$ in the presence of L-NAME completely failed to increase the BMD, in comparison to the OVX rats that received $E_2$ replacement. On the other hand, OVX rats that received NO donor managed to increase their BMD, similar to the rats who received $E_2$ replacement. The BMD in these two groups were similar to that in sham OVX rats, and the combination of $E_2$ and NO donor (NG) was not additive.

Figure 2:
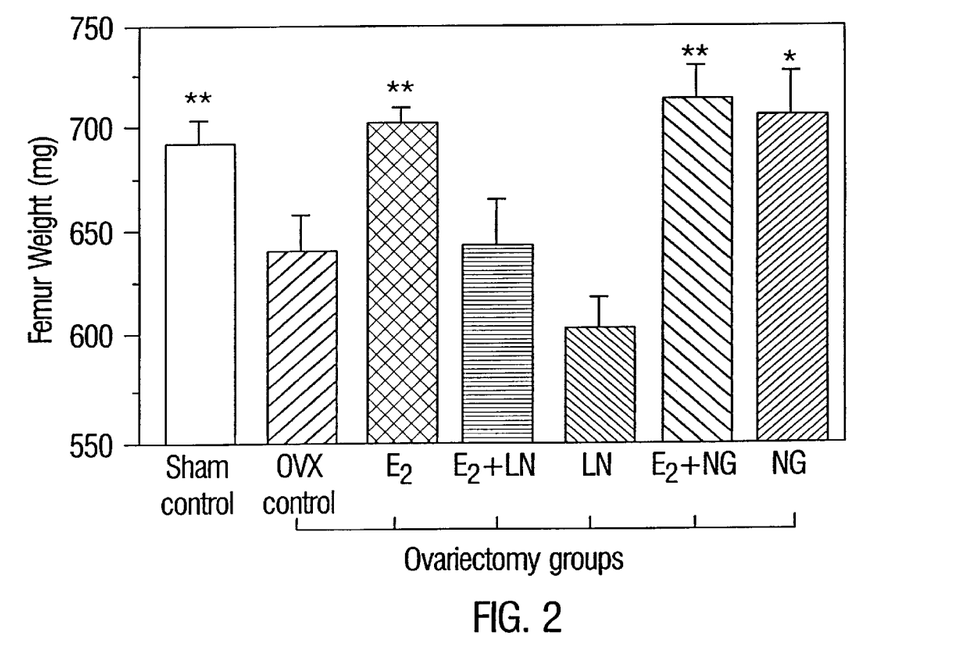
FIG. 2 shows the weights of femurs in rats following various treatments for 6 weeks.

FIG. 2 shows the weights of femurs in rats following various treatments for 6 weeks. OVX=ovariectomy, $E_2$=estrogen treated, LN=L-NAME treated, NG=nitroglycerine treated. Values are mean±SEM of right and left femurs from 5 animals per group. Comparisons were made against ovariectomized rats (reference, OVX control) * P<0.05, * * P<0.02. Femoral weights in OVX rats were substantially lower (P<0.02) compared to sham-operated rats. The OVX-induced decrease in femoral weight was reversed by $E_2$ (P<0.02), and also by NO donor treatment (P<0.05). Again as with BMD, the $E_2$ effect to increase bone weight was blocked by L-NAME. NO donor alone restored the bone weights in OVX rats to the levels of $E_2$ treated OVX and sham-operated (control) rats.

Figure 3:
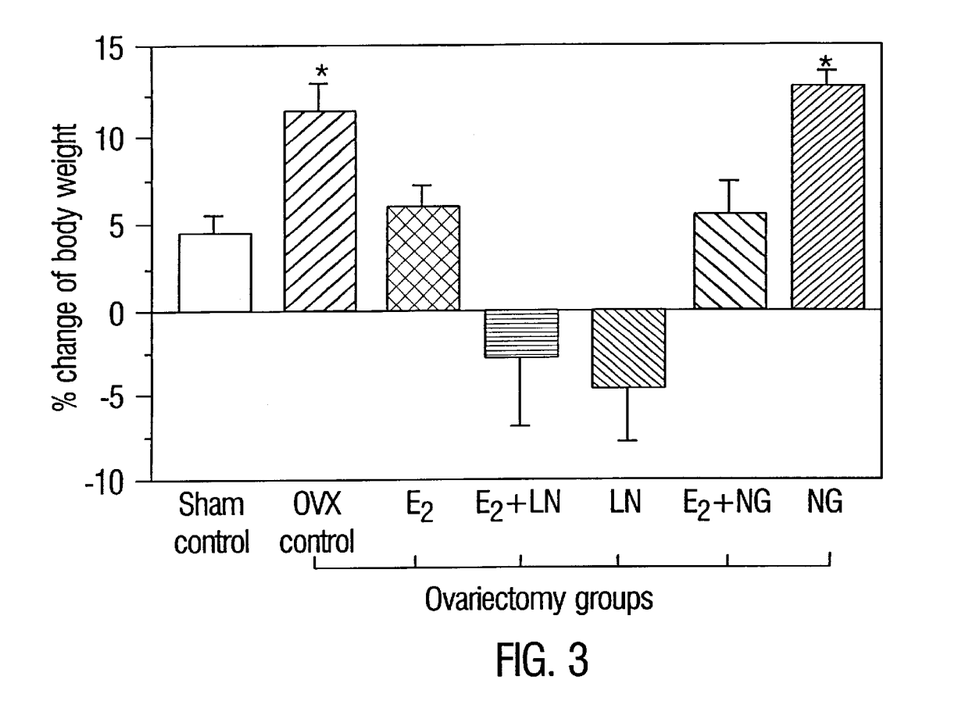
FIG. 3: Percentage changes of body weight over 6 weeks treatment period in various treatment groups.

FIG. 3: Percentage changes of body weight over 6 weeks treatment period in various treatment groups: OVX=ovariectomy, $E_2$=estrogen treated, LN=L-NAME treated, NG=nitroglycerine treated. Values are mean±SEM for 5 animals per group. Comparisons were made against sham-operated rats (control) * P<0.01. As expected OVX increased the body weight (due to the increase in total body fat, P<0.01), and this was prevented by $E_2$ replacement alone or combination of estrogen with nitroglycerine. There was a tendency to lose some weight in L-NAME treated rats, but this was not statistically different to that observed with the sham-operated as well as estrogen treated rats. The weight of rats receiving NG alone had a similar increase in weight to that observed with OVX rats.

Surgical or natural menopause in women leads to both cortical and trabecular bone loss (S. J. Wimalawansa, 1993). Osteoporosis induced by OVX in rats has been widely used as a model of postmanopausal osteoporosis (D. N. Kalu, 1991) and has been validated as a clinically relevant model of human postmenopausal bone loss (Wronski et al., 1993).

Our data demonstrate that, treatment with NO protects against the OVX-induced bone loss in adult female rats, as determined by DXA BMD measurements and bone weights. Our study shows that OVX for 6 weeks in 12 week old female rats decreased the increment of BMD (P<0.02), and this was prevented with either $E_2$ replacement or administration of a NO donor. Moreover, it is likely that the $E_2$-induced increase in BMD is dependent upon NO generation, since L-NAME completely obliterated the effects of estradiol. These studies indicate that exogenous NO can reverse the bone loss in estradiol-deficit animals and that estradiol-induced increase in BMD may be NO dependent.

Our studies suggest that exogenously administered NO may have therapeutic value in preventing the bone loss accompanying estrogen deficiency. These studies emphasize the potential importance of NO in regulating bone mineral metabolism. The fact that nitroglycerine, when administered topically can prevent bone loss suggests the possible usefulness of NO donors as therapy (i.e., simple and effective mode of delivery) for preventing bone loss in postmenopausal women.

Without further elaboration, it is believed that one skilled in the art can, using the preceding description, utilize the present invention to its fullest extent. The preferred specific embodiments are, therefore, to be construed as merely illustrative, and not limitative of the disclosure in any way whatsoever. The entire disclosure of all applications, patents and publications, cited above and below are hereby incorporated by reference.

EXAMPLE 1

Treatment of Osteoporosis and Other Metabolic Bone Disorders

To a nonpregnant human female (ca 45 years; 50–80 kg) displaying the signs of menopause or postmenopausal osteoporosis (primary and secondary) and/or other metabolic bone disorders, or to a human male displaying signs of osteoporosis and/or other metabolic bone disorders, administer L-arginine initially with a dose range of 0.5 to 20 g of L-arginine per os daily in three divided doses followed by a daily dose of 0.5 to 5 g of L-arginine.

EXAMPLE 2

Treatment of Osteoporosis and Other Metabolic Bone Disorders

To a female or male comparable to Example 1, administer daily 2×2.5 mg of nitroglycerine.

EXAMPLE 3

Treatment of Osteoporosis and Other Metabolic Bone Disorders

To a female comparable to Example 1, administer daily 0.5 to 20 g of L-arginine in combination with estrogen (e.g. estradiol valerate) 1–2 mg daily.

EXAMPLE 4

Treatment of Osteoporosis and Other Metabolic Bone Disorders

To a female comparable to Example 1, administer daily 2×2.5 mg nitroglycerine with a progestin (e.g. norgestrel) 150 µg per day.

EXAMPLE 5

Treatment of Osteoporosis and Other Metabolic Bone Disorders

To a male comparable to Example 1, administer daily 0.5 to 20 g of L-arginine in combination with suitable depot preparation of an androgen.

EXAMPLE 6

Treatment of Osteoporosis and Other Metabolic Bone Disorders

To a male comparable to Example 1, administer daily 2×2.5 mg nitroglycerine with a suitable depot preparation of an androgen.

EXAMPLE 7

Treatment of Osteoporosis and Other Metabolic Bone Disorders

To a female comparable to Example 1, administer L-arginine 0.5 to 20 g daily and/or a nitric oxide donor (e.g. nitroglycerine, 2×2.5 mg) daily with or without one of the following, an estrogen (e.g. estradiol valerate) 1–2 mg daily, or a progestin (e.g. norgestrel, at 150 µg per day) or an androgen, respectively.

The preceding examples can be repeated with similar success by substituting the generically or specifically described reactants (bisphosphonate, calcitonin, anabolic steroids, fluoride) and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for prevention or treatment of primary and secondary osteoporosis of a female or male mammal comprising administering to the susceptible or afflicted mammal at least one of L-arginine effective to raise the blood level of circulating L-arginine to at least about 1 mM above the normally circulating levels or a nitric oxide donor in an amount producing a level of nitric oxide about equivalent to that produced by the elevated L-arginine levels.

2. The method of claim 1, where the mammal is female, further comprising administration of at least one of an estrogen and progestin.

3. The method of claim 1, where the mammal is male, further comprising administration of an androgen.

4. The method of claim 1 further comprising administration of an agent affecting bone metabolism.

5. The method of claim 4 where the agent is at least one of calcitonin, anabolic steroid and fluoride.

6. The method of claim 1, wherein the mammal is a female human suffering from primary or secondary osteoporosis.

7. The method of claim 1, wherein the mammal is a female human subject to hormone replacement therapy, a candidate for hormone replacement therapy or for osteoporosis therapy.

8. The method of claim 1 wherein the mammal is a male human having osteoporosis or being a candidate for osteoporosis therapy.

9. The method of claim 1, wherein the mammal is a human and L-arginine is administered thereto.

10. The method of claim 1, wherein the mammal is a human and a nitric oxide donor is administered thereto.

11. The method of claim 10, wherein the nitric oxide donor is sodium nitroprusside, nitroglycerine, SIN-1, isosorbidmononitrite or isosorbiddinitrite.

12. The method of claim 10, wherein the nitric oxide donor is administered orally or parenterally.

13. The method of claim 10 where the administration is transdermal, by inhalation, percutaneous, intravenous, intramuscular, subcutaneous, depot preparation, sublingual or rectal.

14. The method of claim 1, wherein the mammal is a human female and the L-arginine or nitric oxide donor is administered in combination with an estrogen.

15. The method of claim 14, wherein the estrogen is estradiol valerate, conjugated equine estrogens, 17b-estradiol, estrone or estriol.

16. The method of claim 14 where the estrogen is an estrogen analog and an antiestrogen.

17. The method of claim 1, wherein the mammal is a female human and the L-arginine or nitric oxide donor is administered in combination with a progestin.

18. The method of claim 17, wherein the progestin is progesterone, dyprogesterone, medroxyprogesterone, norethisterone, levonorgestrel, or norgestrel.

19. The method of claim 17 where the progestin is a progestational compound or progestin analog.

20. The method of claim 2, wherein the mammal is a female human and the estrogen or progestin are administered continuously.

21. The method of claim 2, wherein the mammal is a female human and the estrogen or progestin is administered cyclically.

22. The method of claim 1, wherein the mammal is a human and the L-arginine or nitric acid donor is administered in combination with calcitonin.

23. The method of claim 22, wherein the calcitonin is salmon calcitonin, eel calcitonin, human calcitonin, α calcitonin, β calcitonin or calcitonin analog.

24. The method of claim 1, wherein the mammal is a human and the L-arginine or nitric oxide donor is administered in combination with a fluoride salt.

25. The method of claim 24, wherein the fluoride salt is a rapid or slow release sodium fluoride formulation.

26. The method of claim 1, wherein the mammal is a human and the L-arginine or nitric oxide donor is administered in combination with an anabolic steroid.

27. The method of claim 26, wherein the anabolic steroid is nondrolone decanoate.

28. The method of claim 5 wherein the mammal is a human and calcitonin, fluoride, or anabolic steroid is administered continuously.

29. The method of claim 5 wherein the mammal is a human and calcitonin or fluoride is administered cyclically.

30. The method of claim 1 wherein the male mammal is a human and L-arginine or nitric acid donor is administered in combination with an androgen.

31. The method of claim 30, wherein the androgen is testosterone.

32. The method of claim 3 wherein the mammal is a male human and the androgen is administered continuously.

33. The method of claim 3, wherein the mammal is a male human and the androgen is administered cyclically.

34. A pharmaceutical composition comprising (a) at least one of L-arginine and a nitric oxide donor, and (b) at least one of, an estrogen, a progestin, a calcitonin, a fluoride, an anabolic steroid, or an androgen.

35. The composition of claim 34 wherein L-arginine is in an amount effective to raise blood level of circulating L-arginine to at least about 10–50 nM above normally circulating levels upon administration to a patient.

36. The composition of claim 34 wherein the nitric oxide donor is in an amount effective, upon administration to raise nitric oxide levels to about 1–1000 nmolar.

37. The composition of claim 34 wherein estrogen is in an amount equivalent to 1–2 mg of estradiol.

38. The composition of claim 34 wherein the progestin is in an amount bioequivalent to 50–300 mg of injected progesterone.

39. The composition of claim 34 wherein calcitonin is in an amount equivalent to 10–200 I.U. of human calcitonin.

40. The composition of claim 34 wherein fluoride is in an amount equivalent to 10–50 mg of sodium fluoride.

41. The composition of claim 34 wherein anabolic steroid is in an amount equivalent to 50 mg of nondrolone decanoate, and androgens are in an amount equivalent to 100 mg of testosterone.

42. The composition according to claim 34, wherein L-arginine is present.

43. The composition according to claim 34, wherein a nitric oxide donor is present.

44. The composition according to claim 43, wherein the nitric oxide donor is sodium nitroprusside, nitroglycerine, glyceryltrinitrate, SIN-1, isosorbidmononitrate or isosorbiddinitrate.

45. The composition according to claim 34, wherein the estrogen is natural or synthetic estrogen or antiestrogen.

46. The composition according to claim 34, wherein the progestin is norgestrel.

47. The composition according to claim 34, wherein the calcitonin is human, salmon or eel calcitonin.

48. The composition according to claim 34, wherein the fluoride is sodium fluoride or a slow release fluoride preparation.

49. The composition according to claim 34, wherein the anabolic steroid is nondrolone decanoate.

50. The composition according to claim 34, wherein the androgen is testosterone.

51. A method for prevention or treatment of primary and secondary osteoporosis comprising administering a nitric oxide donor in an amount effective to provide a level of nitric oxide donor of about 1–1000 nM to a female or male mammal susceptible to or suffering from primary or secondary osteoporosis.

52. The method of claim 51, where the mammal is female, further comprising administration of at least one of an estrogen and progestin.

53. The method of claim 51, where the mammal is male, further comprising administration of an androgen.

54. The method of claim 51, further comprising administration of an agent affecting bone metabolism.

55. The method of claim 54, wherein the agent is at least one of a calcitonin, anabolic steroid and fluoride.

56. The method of claim 51, wherein the mammal is a female human suffering from primary or secondary osteoporosis.

57. The method of claim 51, wherein the mammal is a female human subject to hormone replacement therapy, a candidate for hormone replacement therapy or for osteoporosis therapy.

58. The method of claim 51, wherein the mammal is a male human having osteoporosis or being a candidate for osteoporosis therapy.

59. The method of claim 51, wherein the nitric oxide donor may be selected from the group consisting of sodium nitroprusside, nitroglycerine, SIN-1, isosorbidmononitrite and isosorbiddinitrite.

60. The method of claim 51, wherein the nitric oxide donor is administered orally or parenterally.

61. The method of claim 51, wherein the nitric oxide donor is administered transdermally, by inhalation, percutaneously, intravenously, intramuscularly, subcutaneously, by depot preparation, sublingually or rectally.

62. The method of claim 52, wherein the nitric oxide donor is administered in combination with an estrogen.

63. The method of claim 62, wherein the estrogen may be selected from the group consisting of estradiol valerate, conjugated equine estrogens, 17b-estradiol, estrone and estriol.

64. The method of claim 62, wherein the estrogen is an estrogen analog and an antiestrogen.

65. The method of claim 52, wherein the nitric oxide donor is administered in combination with a progestin.

66. The method of claim 65, wherein the progestin be selected from the group consisting of progesterone, dyprogesterone, medroxyprogesterone, norethisterone, levonorgestrel and norgestrel.

67. The method of claim 65, wherein the progestin is a pregestational compound or progestin analog.

68. The method of claim 52, wherein the estrogen or progestin are administered continuously.

69. The method of claim 52, wherein the estrogen or progestin is administered cyclically.

70. The method of claim 55, wherein the nitric oxide donor is administered in combination with a calcitonin.

71. The method of claim 70, wherein the calcitonin be selected from the group consisting of salmon calcitonin, eel calcitonin, human calcitonin, α calcitonin, β calcitonin and calcitonin analog.

72. The method of claim 55, wherein the nitric oxide donor is administered in combination with a fluoride salt.

73. The method of claim 72, wherein the fluoride salt is a rapid or slow release sodium fluoride formulation.

74. The method of claim 55, wherein the nitric oxide donor is administered in combination with an anabolic steroid.

75. The method of claim 74, wherein the anabolic steroid is nondrolone decanoate.

76. The method of claim 55, wherein the calcitonin, fluoride or anabolic steroid is administered continuously.

77. The method of claim 55, wherein the calcitonin, fluoride or anabolic steroid is administered cyclically.

78. The method of claim 53, wherein the androgen is testosterone.

79. The method of claim 53, wherein the androgen is administered continuously.

80. The method of claim 53, wherein the androgen is administered cyclically.

81. A pharmaceutical composition comprising a nitric oxide donor and at least one compound selected from the group consisting of an estrogen, a progestin, a calcitonin, a fluoride, an anabolic steroid, and an androgen.

82. The composition of claim 81, wherein the nitric oxide donor is in an amount effective to raise nitric oxide levels to about 1–1000 molar upon administration.

83. The composition of claim 81, further comprising an estrogen.

84. The composition of claim 83, wherein the estrogen is natural or synthetic estrogen or antiestrogen.

85. The method of claim 83, wherein the estrogen is in an amount equivalent to 1–2 mg of estradiol.

86. The composition of claim 81, further comprising a progestin.

87. The composition of claim 86, wherein the progestin is norgestrel.

88. The composition of claim 86, wherein the progestin is in an amount bioequivalent to 50–300 mg of injected progesterone.

89. The composition of claim 81, further comprising calcitonin.

90. The composition of claim 89, wherein the calcitonin be human, salmon or eel calcitonin.

91. The composition of claim 89, wherein the calcitonin is in an amount equivalent to 10–200 I.U. of human calcitonin.

92. The composition of claim 81, further comprising fluoride.

93. The composition of claim 92, wherein the fluoride be sodium fluoride or a slow release fluoride preparation.

94. The composition of claim 92, wherein the fluoride is in an amount equivalent to 10–50 mg of sodium fluoride.

95. The composition of claim 81, further comprising an anabolic steroid and androgen.

96. The composition of claim 95, wherein the anabolic steroid is nondrolone decanoate and the androgen is testosterone.

97. The composition of claim 95, wherein the anabolic steroid is in an amount equivalent to 50 mg of nondrolone decanoate and androgen is in an amount equivalent to 100 mg of testosterone.

98. The composition of claim 81, wherein the nitric oxide donor be selected from the group consisting of sodium nitroprusside, nitroglycerine, glyceryltrinitrate, SIN-1, isosorbidmononitrate and isosorbiddinitrate.

* * * * *

UNITED STATES PATENT AND TRADEMARK OFFICE
CERTIFICATE OF CORRECTION

PATENT NO. : 6,133,320
DATED : October 17, 2000
INVENTOR(S) : Yallampalli

It is certified that error appears in the above-identified patent and that said Letters Patent is hereby corrected as shown below:

In claim 34, column 11, line 66, please delete "one of, an" and insert -- one of an -- therefor.

In claim 34, column 11, line 67, please delete "or" and insert -- and -- therefor.

In claim 84, column 14, line 14, please delete "method" and insert -- composition-- therefor.

In claim 66, column 13, line 20, please delete "be" and insert --is -- therefor.

In claim 71, column 13, line 32, please delete "be" and insert --is -- therefor.

In claim 90, column 14, line 27, please delete "be" and insert --is -- therefor.

In claim 93, column 14, line 33, please delete "be" and insert --is -- therefor.

In claim 98, column 14, line 48, please delete "be" and insert --is -- therefor.

Signed and Sealed this

Twenty-second Day of May, 2001

Attest:

NICHOLAS P. GODICI

Attesting Officer

Acting Director of the United States Patent and Trademark Office